United States Patent
Furuta

(10) Patent No.: US 12,304,368 B2
(45) Date of Patent: May 20, 2025

(54) VEHICLE CONTROL DEVICE

(71) Applicant: TOYOTA JIDOSHA KABUSHIKI KAISHA, Toyota (JP)

(72) Inventor: Hiroki Furuta, Shizuoka-ken (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 0 days.

(21) Appl. No.: 18/397,593

(22) Filed: Dec. 27, 2023

(65) Prior Publication Data

US 2024/0253541 A1    Aug. 1, 2024

(30) Foreign Application Priority Data

Jan. 31, 2023 (JP) ................ 2023-013016

(51) Int. Cl.
| | | |
|---|---|---|
| *B60N 2/50* | (2006.01) | |
| *A61B 5/16* | (2006.01) | |
| *B60N 2/02* | (2006.01) | |
| *B60G 17/00* | (2006.01) | |
| *B60N 2/00* | (2006.01) | |
| *B60N 2/90* | (2018.01) | |

(52) U.S. Cl.
CPC ............ *B60N 2/501* (2013.01); *A61B 5/16* (2013.01); *B60N 2/0273* (2023.08); *B60N 2/502* (2013.01); *B60G 17/00* (2013.01); *B60N 2/002* (2013.01); *B60N 2/90* (2018.02); *B60N 2002/981* (2018.02)

(58) Field of Classification Search
CPC ........ B60N 2/501; B60N 2/502; B60N 2/544; B60N 2/0273; B60N 2/002; B60N 2/0268; B60N 2/0244; B60N 2/90; B60N 2002/98; A61B 5/16; A61B 5/0048; B60G 17/00
See application file for complete search history.

(56) References Cited

U.S. PATENT DOCUMENTS

| | | | |
|---|---|---|---|
| 10,379,535 B2 * | 8/2019 | Migneco | A61B 5/746 |
| 2003/0151516 A1 * | 8/2003 | Basir | G08B 21/06 |
| | | | 600/300 |
| 2006/0261647 A1 | 11/2006 | Maas et al. | |
| 2021/0290134 A1 * | 9/2021 | Talamonti | A61B 5/37 |
| 2024/0198750 A1 * | 6/2024 | Furuta | B60G 17/0165 |

FOREIGN PATENT DOCUMENTS

| | | | | |
|---|---|---|---|---|
| DE | 102019204892 A1 * | 10/2020 | .......... | B60K 28/066 |
| JP | 2006-509673 A | 3/2006 | | |
| JP | 2017056042 A * | 3/2017 | .......... | A61B 5/0205 |
| WO | WO-2019182033 A1 * | 9/2019 | | |

* cited by examiner

*Primary Examiner* — Tan Le
(74) *Attorney, Agent, or Firm* — Sughrue Mion, PLLC

(57) ABSTRACT

A vehicle control device includes a vibration information detection device that detects information relating to vibration of a seat, a drowsiness detection device that detects a state related to drowsiness of an occupant in the seat, and a controller that controls an active suspension. The controller includes a processor. The processor determines, based on detection results from the drowsiness detection device, whether a specific occupant, who is an occupant that is not a driver during manual driving, is asleep or falling asleep. When determining that the specific occupant is asleep or falling asleep, and determining that the vibration of the seat is less than the predetermined value, the processor controls the active suspension such that the vibration of the seat is no less than the predetermined value.

10 Claims, 2 Drawing Sheets

VEHICLE CONTROL DEVICE

CROSS-REFERENCE TO RELATED APPLICATION

This application claims priority to Japanese Patent Application No. 2023-013016 filed on Jan. 31, 2023, incorporated herein by reference in its entirety.

BACKGROUND

1. Technical Field

The present disclosure relates to a vehicle control device that controls an active suspension.

2. Description of Related Art

In some vehicles, an active suspension is disposed between a seat and a vehicle body in order to suppress vibration of the seat of the vehicle. The active suspension controls force acting between the seat and the vehicle body. A controller controls the active suspension, so as to suppress vibration of the seat in response to vibration input to the seat. For example, Japanese Unexamined Patent Application Publication (Translation of PCT Application) No. 2006-509673 (JP 2006-509673 A) describes an active suspension provided in a seat and having two degrees of freedom of movement.

The active suspension is controlled to suppress vibration of the seat. However, there are cases in which an occupant who is asleep or is falling asleep in the seat will be more comfortable with a certain amount of vibration.

SUMMARY

The present disclosure provides a vehicle control device that is capable of maintaining and improving comfort for specific occupants asleep or falling asleep.

According to an aspect of the present disclosure, a vehicle control device includes an active suspension including an actuator which is interposed between a seat of a vehicle and a vehicle body and which is configured to change a relative position of the seat with respect to the vehicle body, a vibration information detection device configured to detect information related to vibration of the seat, a drowsiness detection device configured to detect a state related to drowsiness of an occupant seated in the seat, and a controller configured to control the active suspension. The controller includes a processor. The processor is configured to determine, based on detection results from the drowsiness detection device, whether a specific occupant who is the occupant that is not a driver during manual driving is asleep or falling asleep. Also, the processor is configured to determine whether the vibration of the seat is less than a predetermined value based on detection results from the vibration information detection device. Also, the processor is configured to control the active suspension such that the vibration of the seat is no less than the predetermined value when determining that the specific occupant is asleep or falling asleep and determining that the vibration of the seat is less than the predetermined value.

According to the present disclosure, when an occupant who is not a driver (specific occupant) during manual driving is asleep or falling asleep in the seat, vibration of the seat is maintained at no less than a predetermined value. It is known that the occupant is more likely to go to sleep in a seat in which predetermined vibration is generated, than in a seat that is not vibrating. For example, when speed of the vehicle decreases in a state in which the specific occupant is asleep, and the vibration of the seat becomes small, the specific occupant may sleep less deeply, and finally wake up. However, according to the present disclosure, the vibration of the seat is maintained at no less than the predetermined value in a specific state, and accordingly the comfort of the specific occupant asleep or falling asleep in the seat can be maintained/improved.

BRIEF DESCRIPTION OF THE DRAWINGS

Features, advantages, and technical and industrial significance of exemplary embodiments of the present disclosure will be described below with reference to the accompanying drawings, in which like signs denote like elements, and wherein.

DETAILED DESCRIPTION OF EMBODIMENTS

Hereinafter, a vehicle control device that is an embodiment of the present disclosure will be described in detail with reference to the drawings, as a form for carrying out the present disclosure. Note that in addition to the embodiment described below, the present disclosure can be carried out in various forms with various modifications and improvements made thereto, based on the knowledge of one skilled in the art.

Figure 1:
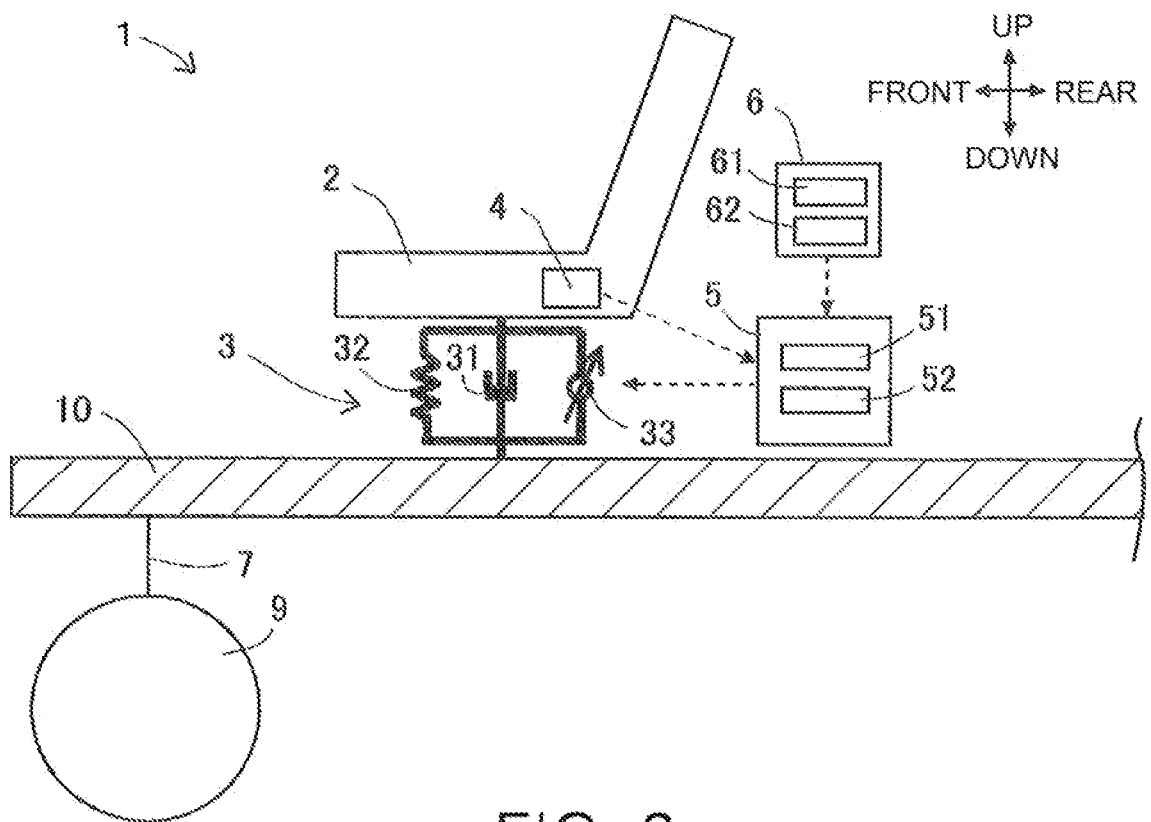
FIG. 1 is a configuration diagram of a vehicle control device according to an embodiment.

As illustrated in FIG. 1, a vehicle control device 1 includes an active suspension 3, a vibration information detection device 4, a controller 5 and a drowsiness detection device 6. The active suspension 3 is disposed between a seat 2 and a vehicle body 10. The active suspension 3 is installed on a bottom forming member of the vehicle body 10, for example. The active suspension 3 is configured so as to be capable of controlling force acting between the seat 2 and the vehicle body 10. The active suspension 3 is configured so as to be capable of controlling, for example, a relative position of the seat 2 relative to the vehicle body 10 (e.g., moving force or holding force), damping force between the vehicle body 10 and the seat 2, and spring constant (elastic force) between the vehicle body 10 and the seat 2. The active suspension 3 includes an actuator 33 and is configured to be capable of adjusting at least the relative position (displacement amount) of the seat 2 with respect to the vehicle body. The seat 2 connected to the active suspension 3 is also referred to as an "active seat".

To conceptually describe an example of the active suspension 3, the active suspension 3 includes a shock absorber 31 serving as a damper element, a suspension spring 32 serving as a spring element, and an actuator 33. The actuator 33 changes the relative position of the seat 2 in an up-down direction, relative to the vehicle body 10. The seat 2 is moved in the up-down direction by being driven by the actuator 33. The actuator 33 has an electric motor serving as a drive source, and a speed reduction mechanism. Note that the drive source for the actuator 33 may be a hydraulic drive source, for example. One or more actuators 33 are installed for one seat 2. Note that by disposing a plurality of actuators 33 in one seat 2 at a distance from each other, the seat 2 can be tilted and, for example, swaying in a roll direction and swaying in a pitch direction can be countered.

The shock absorber 31 generates a damping force between the vehicle body 10 and the seat 2. The shock absorber 31 may be of a variable type of which the damping force (which may be a damping coefficient or a damping ratio) can be changed, or of a non-variable type of which the damping force cannot be changed. The suspension spring 32 generates elastic force between the vehicle body 10 and the seat 2, in accordance with the spring constant. The suspension spring 32 may be of a variable-spring-constant type or of a non-variable-spring-constant type. The active suspension 3 may include, for example, a link mechanism (e.g., a configuration like a pantograph) that allows a movable portion of the seat 2 to have freedom only in the up-down direction. In this case, for example, the actuator 33 may be connected in parallel to the shock absorber 31 and the suspension spring 32 that act in accordance with actuation of the link mechanism.

The vibration information detection device 4 is a device that detects information relating to vibration of the seat 2. The vibration information detection device 4 according to the present embodiment is an acceleration sensor that is installed in the seat 2, and that detects acceleration in the up-down direction as information relating to vibration of the seat 2. The vibration information detection device 4 transmits detection results to the controller 5. The controller 5 calculates the acceleration, velocity, or displacement amount of the seat 2, in the up-down direction, as vibration of the seat 2, based on the detection results from the vibration information detection device 4. Note that the vibration information detection device 4 may be a device that detects, for example, acceleration of the vehicle body 10 in the up-down direction, information related to a road surface over which object wheels are planned to travel, or information related to vehicle speed that is the speed of the vehicle, as information relating to vibration of the seat 2 in addition to the above information, which will be described later.

The controller 5 is made up of an electronic control unit (ECU) including one or more processors 51 and one or more memory devices 52. The memory device 52 is communicably connected to the processor 51. The memory device 52 may be internal memory or external memory. The controller 5 is communicably connected to the active suspension 3, the vibration information detection device 4, and the drowsiness detection device 6. When a seating sensor (omitted from illustration), which determines whether an occupant is seated in the seat 2, determines that an occupant is present, for example, the controller 5 controls the active suspension 3 corresponding to the seat 2 determined to be occupied by the occupant.

The controller 5 is configured to control the active suspension 3 based on the detection results of the vibration information detection device 4. The controller 5 controls the active suspension 3 so as to reduce vibration of the seat 2 (normal vibration suppression control, described later). The controller 5 controls the actuator 33 to control the relative position of the seat 2 in the up-down direction. The controller 5 sets a current value of a control current supplied to the actuator 33. The controller 5 supplies the control current to the electric motor of the actuator 33 via a drive circuit (omitted from illustration). The current value of the control current is correlative with expansion/contraction amounts of the actuator 33. The expansion/contraction amounts of the actuator 33, i.e., the displacement amount of the seat 2 due to the actuation of the actuator 33, can be said to be the control amount of the actuator 33.

The drowsiness detection device 6 is a device that detects a state of drowsiness of the occupant seated in the seat 2. More specifically, the drowsiness detection device 6 is a device that detects the state of whether the occupant in the seat 2 is asleep or is falling asleep. The drowsiness detection device 6 according to the present embodiment is an image sensor that is provided inside a vehicle cabin and captures images of the occupant in the seat 2. The drowsiness detection device 6 determines a drowsiness level of the occupant based on the image-capturing data of the occupant in the seat 2. The drowsiness level is set to include, for example, at least three stages of "asleep", "falling asleep (sleepy)", and "not asleep (no sleepiness at all)".

More specifically, the drowsiness detection device 6 includes a camera 61 that captures images of the occupant, and an ECU 62 that determines the drowsiness level based on the image-capturing data. The camera 61 is installed on a rearview mirror, a dashboard, an instrument panel, or the like, for example, inside the vehicle cabin of the vehicle. The camera 61 detects the state of the occupant. The ECU 62 uses a known drowsiness estimation algorithm to evaluate the drowsiness state of the occupant, from the image-capturing data of the occupant (e.g., images of the face of the occupant). For example, the ECU 62 detects a degree of opening of the eyes of the occupant, the number of eye-closing actions, and so forth, from the image-capturing data, and determines a drowsiness level that is set in advance. The drowsiness detection device 6 transmits detection results (determination results) to the controller 5. Note that the drowsiness detection device 6 may be configured to actuate only when the seating sensor determines that there is an occupant. The drowsiness detection device 6 can also be said to be an occupant condition monitor.

Sleep Assistance Control and Normal Vibration Suppression Control

Figure 2:
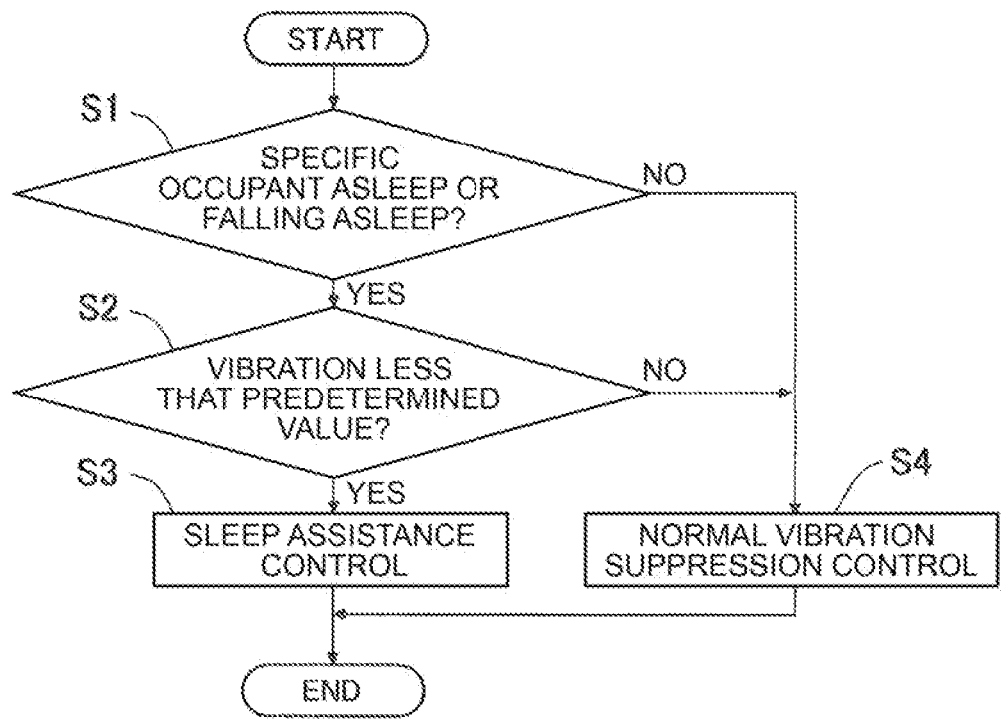
FIG. 2 is a flowchart showing a control example of the vehicle control device according to the embodiment.

As shown in FIG. 2, the controller 5 is configured to execute drowsiness determination processing S1, vibration determination processing S2, sleep assistance control S3, and normal vibration suppression control S4. The drowsiness determination processing S1 is processing in which the controller 5 determines, during manual driving, whether a specific occupant who is not the driver is asleep or is falling asleep, based on the detection results of the drowsiness detection device 6. The specific occupant is a non-driver (passenger), or an occupant sitting in the driver seat during automated driving, during which operations are unnecessary. A specific occupant can also be said to be an occupant who is not driving or an occupant who does not need to drive.

When the detection results (drowsiness level) from the drowsiness detection device 6 correspond to "asleep", the controller 5 determines that the specific occupant in the seat 2 is asleep. When the detection results (drowsiness level) from the drowsiness detection device 6 correspond to "falling asleep", the controller 5 determines that the specific occupant in the seat 2 is falling asleep. Note that the processing of the ECU 62 of the drowsiness detection device 6 may be performed by the controller 5. Also, the ECU 62 may be part of the controller 5.

Also, when each of the active suspensions 3 of a plurality of the seats 2 including the driver seat is an object of control by the controller 5, the controller 5 further determines whether the occupant is the driver, and whether the vehicle is performing automated driving (driving mode that does not require operations by a driver). The controller 5 can execute the determination based on, for example, the detection results from the drowsiness detection device 6, and driving status information. The driving status information is information indicating whether the current driving status is, for example, manual driving or automated driving. The driving status information is stored, for example, in another in-vehicle ECU (e.g., an automated driving ECU) and/or a control system, or the like. The controller 5 acquires driving status information from the in-vehicle ECU and determines whether manual driving or automated driving is being performed.

Whether the occupant is the driver can be determined based on the detection results from the drowsiness detection device 6 (image sensor) and, for example, can also be determined based on the detection results of the seating sensor. The controller 5 determines that the occupant sitting in the driver seat is the driver. The controller 5 is set so as not to execute the sleep assistance control S3 with regard to the seat 2 in which the driver is seated, during manual driving. That is to say, the controller executes the sleep assistance control S3 only for seats 2 in which the specific passengers are seated.

Thus, the drowsiness detection device 6 is an image sensor that captures images of the occupant, and at least one of the drowsiness detection device 6 and the controller 5 determines the drowsiness level of the occupant based on the occupant imaging data. The drowsiness level includes at least three stages of asleep, falling asleep, and not asleep. The controller 5 determines whether the occupant is asleep or falling asleep based on the drowsiness level.

The vibration determination processing S2 is processing in which the controller 5 determines whether the vibration of the seat 2 is less than a predetermined value, based on the detection results from the vibration information detection device 4. The magnitude of vibration can be represented by displacement (amplitude), velocity, or acceleration. The detection results can also be said to be detection values. The controller 5 computes the magnitude of vibration of the seat 2 based on the acceleration of the seat 2 in the up-down direction, detected by the vibration information detection device 4. Based on the detection values from the vibration information detection device 4, the controller 5 can compute the acceleration in the up-down direction, velocity in the up-down direction (first-order time integration of acceleration), and displacement amount in the up-down direction (second-order time integration of acceleration), of the seat 2. The predetermined value is set to acceleration, velocity, or displacement amount (amplitude), in the up-down direction, so as to correspond to this computed value.

Figure 3:
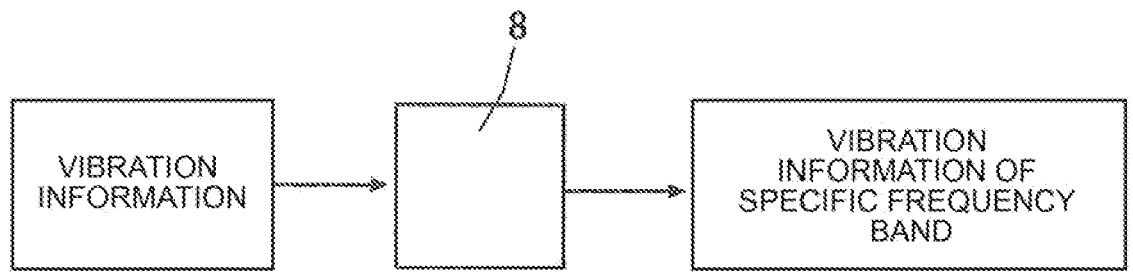
FIG. 3 is a conceptual diagram of a filter of according to the embodiment.

The controller 5 compares, for example, the amplitude of the seat 2 in the up-down direction that is computed, with the predetermined value set as a threshold value of the amplitude. The controller 5 determines whether the amplitude of the computed value is less than the predetermined value. The comparison between the vibration and the predetermined value may be performed for an entire frequency band of vibration, or may be performed just for a specific frequency band of vibration. As illustrated in FIG. 3, vibration in a specific frequency band can be obtained by applying a filter 8 to signals of the vibration. The filter 8 is, for example, a low-pass filter, a high-pass filter, a band-pass filter, or the like.

As an example, it is known that low-frequency vibration promotes drowsiness in infants. Based on this knowledge, the vehicle control device 1 may be configured to apply a low-pass filter to the detection value of the vibration information detection device 4 to detect only vibration in a low frequency band. In this case, the controller 5 determines whether the vibration of the seat 2 in the low frequency band is less than a predetermined value. The vehicle control device 1 may be configured to detect vibration in a specific frequency band, in accordance with knowledge adopted by the designer.

Thus, the controller 5 may determine whether the vibration in the specific frequency band out of the vibration of the seat 2 is less than the predetermined value, based on the detection results from the vibration information detection device 4. In this case, when the controller 5 determines that a specific occupant is asleep or is falling asleep, and determines that the vibration in the specific frequency band of the vibrations of the seat 2 is less than the predetermined value, the active suspension is controlled so that the vibration of the seat 2 in the specific frequency band is no less than the predetermined value. The "vibration of the seat 2" is a concept including "vibration in a specific frequency band out of vibrations of the seat 2".

The normal vibration suppression control S4 is a type of control of the active suspension 3 performed by the controller 5. Specifically, the normal vibration suppression control S4 is active control for the controller 5 to control the active suspension 3 so as to reduce the vibration of the seat 2 based on the detection values of various vehicle-mounted sensors (e.g., the vibration information detection device 4) that detect information relating to vibration. For example, the normal vibration suppression control S4 is feedback control in which the controller 5 controls the active suspension 3 so that the detection value or the computed value of the vehicle-mounted sensor approaches a target value.

When the normal vibration suppression control S4 is executed, the detection values of the acceleration sensor (vibration information detection device 4) installed in the seat 2 are values reduced by the active suspension 3. The in-vehicle sensor used for the normal vibration suppression control S4 is not limited to the vibration information detection device 4, and may be an acceleration sensor for detecting acceleration in the up-down direction, a vehicle height sensor, or the like, installed on the vehicle body 10. Thus, the controller 5 is configured to execute normal vibration suppression control that controls the active suspension 3 so as to reduce vibration of the seat 2.

The sleep assistance control S3 is a type of control of the active suspension 3 performed by the controller 5. Specifically, the sleep assistance control S3 is control that is performed when the controller 5 determines that the specific occupant is asleep or is falling asleep and also determines that the vibration of the seat 2 is less than a predetermined value, so as to control the active suspension 3 such that the vibration of the seat 2 is no less than the predetermined value. Note that the target value of the vibration of the seat 2 in the sleep assistance control S3 may be set to a predetermined value. In this case, in the sleep assistance control S3, the active suspension 3 is controlled so that the vibration of the seat 2 is the predetermined value. The sleep assistance control S3 of the present embodiment is executed along with the normal vibration suppression control S4. Hereinafter, a case in which the controller 5 determines that the specific occupant is asleep or is falling asleep and also determines that the vibration of the seat 2 is less than a predetermined value will also be referred to as "predetermined case".

The controller 5 executes vibration addition processing and/or control amount adjustment processing, in order to set the vibration of the seat 2 to no less than the predetermined value in the predetermined case. The vibration addition processing is processing in which the controller 5 controls the actuator 33 to add a certain vibration (predetermined vibration) to the seat 2 so that the vibration of the seat 2 is no less than the predetermined value. In the predetermined case, the controller 5 uses the actuator 33 to add vibration to the seat 2 as vibration addition processing so that the vibration of the seat 2 is no less than the predetermined value.

The controller 5 can comprehend the vibration state (amplitude, velocity, acceleration, frequency, etc.) of the seat 2 based on the detection value of the vibration information detection device 4. Comparison between the vibration and the predetermined value can be executed, for example, by standardizing the values of both by the amplitude, velocity, or acceleration, of the vibration, and comparing the magnitudes of both.

As an example of vibration addition processing, the controller 5 computes the difference between the current vibration and a predetermined value, i.e., the amount of vibration that is lacking for sleep assistance. The controller 5 controls the actuator 33 based on the amount of vibration that is lacking. For example, the controller 5 may add a control amount corresponding to the amount of vibration that is lacking, to the control amount of the normal vibration suppression control S4, and control the actuator 33. The controller 5 may add just vibrations in the up-down direction to the seat 2. The reason is that because it is known that when the seat 2 is subjected to vibration in the roll direction or vibration in the pitch direction, the head of the occupant tends to move, and comfort of the occupant decreases.

In the vibration adding processing, the controller 5 may control the actuator 33 so that amplitude thereof is increased in-phase with the current vibration of the seat 2 in the up-down direction. When the seat 2 is vibrating with a small amplitude due to execution of the normal vibration suppression control S4 or without execution of the normal vibration suppression control S4, vibration addition processing is executed to add upward force to the seat 2 by the actuator 33 at a timing matching the timing of the seat 2 moving upward. Similarly, when the seat 2 moves downward, the actuator 33 adds downward force to the seat 2. Thus, the vibration amplitude of the seat 2 increases. The controller 5 controls the actuator 33 to match or not match the vibration, resulting in desired vibration being generated in the seat 2. The controller 5 may add just vibration in a specific frequency band to the seat 2 in the vibration adding processing.

The control amount adjustment processing is processing for the controller 5 to adjust the control gain used in computation of the control amount of the actuator 33 in the normal vibration suppression control S4, or is processing for adjusting the control amount. The control amount corresponds to the value of the control current supplied to the electric motor of the actuator 33, for example. In the normal vibration suppression control S4, for example, the controller 5 computes state quantity (e.g., displacement amount) of the seat 2 based on the detected vibration, and multiplies the state quantity by the control gain to calculate the control amount. The controller 5 can adjust the control amount of the actuator 33 by adjusting the value of the control gain (0<control gain≤1). For example, the smaller the control gain is, the smaller the control amount is.

When the vibration is less than the predetermined value as a result of executing the normal vibration suppression control S4, the controller 5 reduces the control gain so that the vibration of the seat 2 no less than the predetermined value in the control amount adjustment processing. When the control gain becomes small and the control amount of the actuator 33 becomes small, vibration suppression force with respect the input vibration becomes small, and the vibration of the seat 2 becomes great.

In the control amount adjustment processing, the controller 5 may reduce the control gain or the control amount just for vibrations in a specific frequency band. The controller 5 can acquire the control amount for a specific frequency band, by applying a band-pass filter to the control amount in the normal vibration suppression control S4 when the control amount adjustment processing is not performed, for example. The controller 5 may reduce the control amount or may set the control amount to 0 with respect to the control amount of a specific frequency band. When the control amount is set to 0, the normal vibration suppression control S4 is not executed regarding vibration in the specific frequency band. Thus, the controller 5 can reduce or set the control amount to 0 with respect to vibration in a specific frequency band that is considered to contribute to improved comfort.

A control amount $F_{se}$ for the actuator 33 is computed by the following Expressions (1) to (3), as one example. $F_{se1}$ is a lower-side control amount. The lower-side control amount is a control amount for vibration of the vehicle body 10 under the seat 2. $Z_{se1}$ is the displacement amount in the up-down direction of the portion of the vehicle body 10 at which the seat 2 is disposed. $C_{se}$ is a damping coefficient of the shock absorber 31. $k_{se}$ is a spring constant of the suspension spring 32. Properties such as the damping coefficient, the spring constant, and so forth, of the active suspension 3, are set in advance. s is a Laplacian operator. $\alpha_1$ is velocity term gain. $\beta_1$ is displacement term gain. $F_{se2}$ is an upper-side control amount. The upper-side control amount is a control amount for vibration of the seat 2. $Z_{se2}$ is the displacement amount of the seat 2 in the up-down direction. $\alpha_2$ is velocity term gain. $\beta_2$ is displacement term gain. $F_{se}$ is the control amount of the actuator 33 at the point in time of computation. $Z_{se1}$ and $Z_{se2}$ are computed based on the detection results of various in-vehicle sensors, such as an up-down acceleration sensor installed in the seat 2 and/or an up-down acceleration sensor installed in the vehicle body 10, for example. The controller 5 is capable of adjusting any of the control gains $\alpha_1$, $\alpha_2$, $\beta_1$, and $\beta_2$.

$$F_{se1} = \alpha_1 C_{se} Z_{se1} s + \beta_1 k_{se} Z_{se1} \quad (1)$$

$$F_{se2} = \alpha_2 C_{se} Z_{se2} s + \beta_2 k_{se} Z_{se2} \quad (2)$$

$$F_{se} = F_{se1} + F_{se2} \quad (3)$$

Thus, when determining that the specific occupant is asleep or is falling asleep, and determining that the vibration of the seat 2 is less than the predetermined value in a state in which the normal vibration suppression control S4 is being executed, the controller 5 reduces the control amount or the control gain for the actuator 33 in the normal vibration suppression control S4 as control amount adjustment processing, so that the vibration of the seat 2 is no less than the predetermined value.

As shown in FIG. 2, the controller 5 determines whether the specific occupant is asleep or falling asleep, based on the detection results of the drowsiness detection device 6 while executing the normal vibration suppression control S4 (S1). When the controller 5 determines that the specific occupant is asleep or is falling asleep (Yes in S1), the controller 5 determines whether the vibration of the seat 2 is less than the predetermined value, based on the detection results from the vibration information detection device 4 (S2). When the controller 5 determines that the vibration is less than the predetermined value (Yes in S2), the sleep assistance control is executed while continuing the normal vibration suppression control S4 (S3). At least one of the vibration addition processing and the control amount adjustment processing is executed in the sleep assistance control S3. Note that the controller 5 may temporarily suspend the normal vibration suppression control S4 when executing the sleep assistance control S3.

On the other hand, when the controller 5 determines that the specific occupant is neither asleep nor falling asleep (No in S1), or determines that the vibration is no less than the predetermined value (No in S2), the sleep assistance control S3 is not executed, and execution of the normal vibration suppression control is continued (S4). The controller 5 executes such processing every certain amount of time. When the drowsiness determination processing S1 yields No, or when the vibration determination processing S2 yields No, the controller 5 continues to execute the normal vibration suppression control S4. Also, the controller 5 continues to execute the normal vibration suppression control S4 without executing the sleep assistance control S3 for the seat 2 in which the driver is seated during manual driving. The order in which the drowsiness determination processing S1 and the vibration determination processing S2 are executed may be opposite to the order shown in FIG. 2.

According to the present embodiment, when the specific occupant is asleep or is falling asleep in the seat 2, the vibration of the seat 2 is maintained at no less than the predetermined value. It is known that the occupant is more likely to go to sleep in the seat 2 in which the predetermined vibration is generated, than in the seat 2 that is not vibrating. For example, when the vehicle speed decreases in a state in which the specific occupant is asleep and the vibration of the seat 2 becomes small, the specific occupant may sleep less deeply, and finally wake up. However, according to the present embodiment, the vibration of the seat 2 is maintained at no less than the predetermined value, and accordingly the comfort of the specific occupant asleep or falling asleep in the seat 2 can be improved.

For example, even in a vehicle in which the vibration level constantly changes, executing the normal vibration suppression control S4 and the sleep assistance control S3 enables unnecessary energy such as excessive swaying of the occupant to be suppressed, the occupant can be swayed appropriately, and furthermore, the comfort and quality of sleep of the occupant can be improved. According to the control amount adjustment processing, the vibration originally input to the seat 2 is utilized to realize the desired vibration, which is excellent from the perspective of energy efficiency.

First Modification of Vibration Information Detection Device

Figure 4:
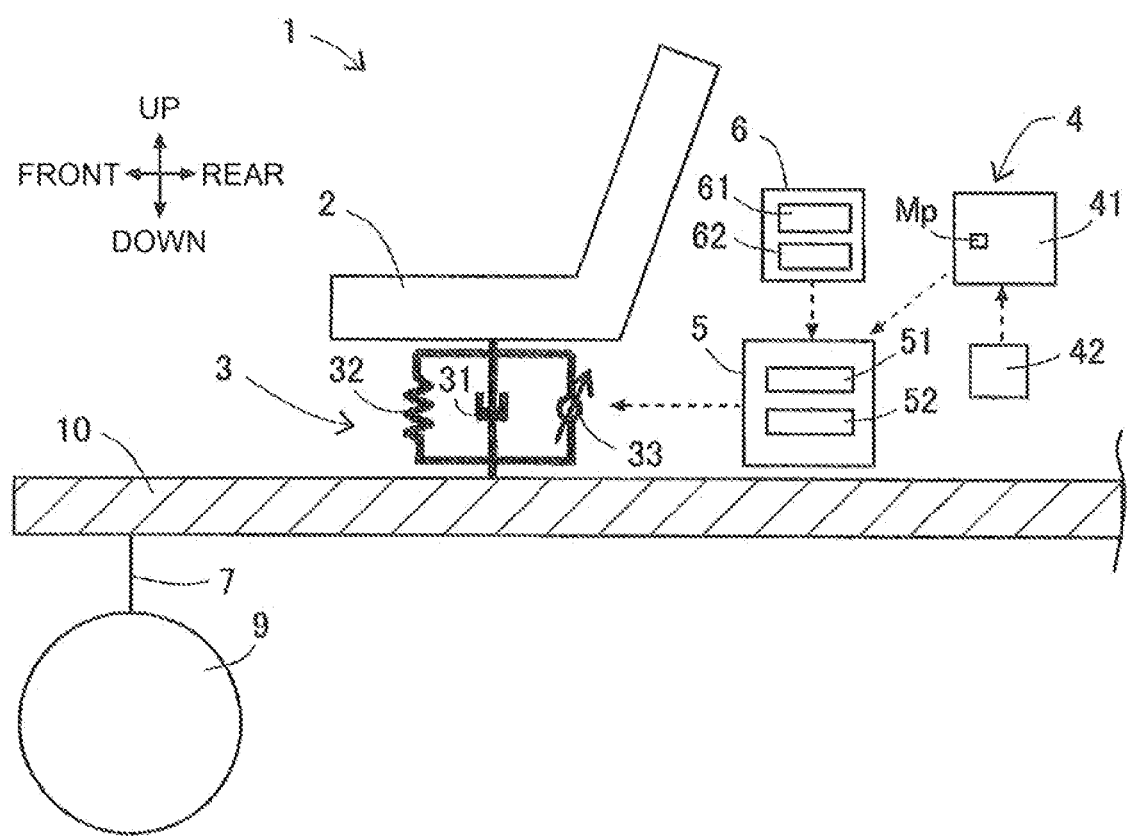
FIG. 4 is a configuration diagram of a first modification of the embodiment.

The vibration information detection device 4 is not limited to the above, and may be, for example, a device that detects information with regard to a planned traveling road surface, which is a road surface over which the object wheels are planned to travel. In this case, as illustrated in FIG. 4, the vibration information detection device 4 includes an ECU 41 having one or more processors and one or more memory devices, and a position detection device 42 for detecting the position of the vehicle. Note that the ECU 41 may be an ECU shared with the controller 5. Also, the memory device may be internal memory or external memory.

In the present embodiment, all wheels 9 are set as being object wheels. The vibration information detection device 4 acquires information regarding the planned traveling road surface (hereinafter, also referred to as "road surface information"). The road surface information includes, for example, displacement of the road surface in the up-down direction, velocity (time derivative value of displacement), and/or acceleration (time derivative value of velocity). That is to say, the road surface information is information related to the displacement in the up-down direction of the planned traveling road surface. Object wheels can be set as appropriate.

The memory of the ECU 41 stores a road surface information map Mp including map information and road surface information correlated with the map information. The road surface information in the road surface information map Mp of the present embodiment is an unsprung state quantity, which is an unsprung state quantity of the vehicle. That is to say, in the road surface information map Mp, the unsprung state quantity and the position on the map are correlated (associated). In the road surface information map Mp, for example, each area of the map information, in which the road is partitioned into areas of a predetermined shape, is correlated with the information regarding the unsprung state quantity. Referring to the road surface information map Mp enables, with respect to a certain position on the map, comprehension of the unsprung state quantity when the vehicle travels at the certain position. The unsprung state quantity is, for example, unsprung displacement amount in the up-down direction, unsprung velocity in the up-down direction, or unsprung acceleration in the up-down direction, for each wheel 9.

The ECU 41 can detect the unsprung state quantity when the vehicle has traveled X meters or after t seconds have elapsed, based on the road surface information map Mp and positional information of the vehicle. The position detection device 42 is installed in the vehicle and includes a receiver that receives vehicle position information from a satellite. The receiver is, for example, a global navigation satellite system (GNSS) receiver. The ECU 41 calculates the unsprung state quantity after t seconds based on, for example, the road surface information map Mp, the position of the vehicle, direction of travel of the vehicle, and the vehicle speed of the vehicle. The ECU 41 transmits the acquired information relating to the unsprung state quantity to the controller 5. The controller 5 executes the normal vibration suppression control S4 after t seconds, based on the unsprung state quantity corresponding to the road surface state after t seconds. That is to say, the controller 5 executes the normal vibration suppression control S4 when the object wheel travels over the planned traveling road surface, based on the unsprung state quantity corresponding to the planned traveling road surface. This normal vibration suppression control S4 can be said to be feedforward control. Such control is referred to as preview vibration suppression control when executed with respect to an active suspension 7 of the suspension.

The controller 5 computes a prediction value, which is the vibration of the seat 2 when the object wheels travel on the planned travel road surface, based on the information relating to the planned traveling road surface. More specifically, based on the detection results of the vibration information detection device 4, the controller 5 calculates the vibration of the seat 2 when the object wheels travel over the planned traveling road surface and the normal vibration suppression control S4 is executed, as a prediction value. The controller 5 determines whether the prediction value is less than a predetermined value.

When determining that the specific occupant is asleep or is falling asleep and determines that the prediction value is less than the predetermined value, the controller 5 controls the active suspension 3 such that the vibration of the seat 2 when the object wheel travels over the planned traveling road surface is no less than the predetermined value (i.e., the sleep assistance control S3 is executed). The same effects as described above are also exhibited by the configuration of this first modification.

Note that when the preview vibration suppression control is executed regarding the active suspension 7 of the suspension, the active suspension 3 is controlled giving consideration thereto in the normal vibration suppression control S4. In this case, the prediction value can be said to be the vibration of the seat 2 that occurs as a result of the preview vibration suppression control and the normal vibration suppression control S4. Moreover, the road surface information may be detection results from a peripheral monitoring device including a camera and/or a LiDAR short for Light Detection and Ranging, or Laser Imaging Detection and Ranging) device, or the like. That is to say, the vibration information detection device 4 may be a peripheral monitoring device. The controller 5 may detect the unevenness of the road surface and so forth based on the detection results from the peripheral monitoring device, and compute the prediction value.

Second Modification of Vibration Information Detection Device

The vibration information detection device 4 is not limited to the above, and may be a device that detects information relating to vehicle speed, such as wheel speed sensors provided on each of the wheels 9, for example. The vehicle speed can be calculated based on the wheel speeds of a plurality of the wheels 9. In this case, in the vibration determination processing S2, the controller 5 determines that the vibration of the seat 2 is less than the predetermined value when the vehicle speed is lower than a predetermined vehicle speed. In general, the vehicle speed and the vibration of the seat 2 have a positive correlative relation. That is to say, in general, the lower the vehicle speed is, the smaller the vibration of the seat 2 is. Thus, the controller 5 may simply determine the magnitude of the vibration of the seat 2 using the vehicle speed. Note that the vehicle speed may be computed based on GNSS information.

Others

The present disclosure is not limited to the embodiment described above. For example, the drowsiness detection device 6 is not limited to the above, and may be a device that transmits a sleep onset signal indicating that the occupant is falling asleep, to the controller 5, in accordance with an operation performed by the occupant. In this case, the controller 5 determines that the occupant is falling asleep when the sleep onset signal is received from the drowsiness detection device 6. The drowsiness detection device 6 may be, for example, a switch that can be operated by the occupant (e.g., a button switch, an on/off switch, a touch panel switch, or the like). The specific occupant turns on the switch when he/she desires to sleep. This satisfies one of the execution conditions of the sleep assistance control S3.

Also, the vibration information detection device 4 may be an acceleration sensor (hereinafter also referred to as "up-down direction acceleration sensor") installed on the vehicle body 10 for detecting acceleration in the up-down direction. The controller 5 may deem the vibration of the vehicle body 10 as being the vibration of the seat 2. Also, the controller 5 may compute the vibration of the seat 2 from the vibration of the vehicle body 10. For example, when three or more up-down direction acceleration sensors are installed at different positions on the vehicle body 10, the controller 5 can calculate the vibration of the seat 2 based on the detection values of these up-down direction acceleration sensors. The controller 5 may also calculate the vibration state (e.g., acceleration, velocity, or displacement amount) of the position of the vehicle body 10 at which the seat 2 is installed. Thus, the vibration information detection device 4 may be an up-down direction acceleration sensor installed in the seat 2 or the vehicle body 10.

The active suspension 3 is installed for at least one of the seats 2. When the seat 2 in which the active suspension 3 is installed is not the driver seat, for example when the active suspension 3 is installed only in a passenger seat, the active suspension 3 is the object of sleep assistance control S3, regardless of the driving mode (automated driving or manual driving). In this case, the controller 5 does not need to determine whether the occupant in the seat 2 is the specific occupant. Also, the controller 5 may be made up of a plurality of ECUs. Also, the term "ECU" in the present disclosure is synonymous with "computer" and can be replaced with "computer." The drowsiness detection device 6 is not limited to an image sensor or a switch, and may be another known device that detects the drowsiness-related state of the occupant (information relating to drowsiness of the occupant).

What is claimed is:

1. A vehicle control device comprising:
an active suspension including an actuator which is interposed between a seat of a vehicle and a vehicle body and which is configured to change a relative position of the seat with respect to the vehicle body;
a vibration information detection device configured to detect information relating to vibration of the seat;
a drowsiness detection device configured to detect a state related to drowsiness of an occupant seated in the seat; and
a controller configured to control the active suspension, wherein the controller includes a processor configured to
determine, based on detection results from the drowsiness detection device, whether a specific occupant who is the occupant that is not a driver during manual driving is asleep or falling asleep,
determine whether the vibration of the seat is less than a predetermined value based on detection results from the vibration information detection device, and
when determining that the specific occupant is asleep or falling asleep, and determining that the vibration of the seat is less than the predetermined value, control the active suspension such that the vibration of the seat is no less than the predetermined value.

2. The vehicle control device according to claim 1, wherein the processor is configured to, when determining that the specific occupant is asleep or falling asleep and determining that the vibration of the seat is less than the predetermined value, add vibration to the seat through the actuator such that the vibration of the seat is no less than the predetermined value.

3. The vehicle control device according to claim 1, wherein the processor is configured to, when determining that the specific occupant is asleep or falling asleep and determining that the vibration of the seat is less than the predetermined value, add vibration to the seat in an up-down direction alone through the actuator such that the vibration of the seat is no less than the predetermined value.

4. The vehicle control device according to claim 1, wherein the processor is configured to
execute normal vibration suppression control for controlling the active suspension to reduce the vibration of the seat, and
when determining that the specific occupant is asleep or falling asleep, and determining that the vibration of the seat is less than the predetermined value in a state in which the normal vibration suppression control is being executed, reduce a control amount or a control gain for the actuator in the normal vibration suppression control such that the vibration of the seat is no less than the predetermined value.

5. The vehicle control device according to claim 1, wherein the processor is configured to
determine whether vibration in a specific frequency band out of vibrations of the seat is less than the predetermined value, based on the detection results of the vibration information detection device, and
when determining that the specific occupant is asleep or falling asleep, and determining that the vibration in the specific frequency band out of vibrations of the seat is less than the predetermined value, control the active suspension such that the vibration of the seat in the specific frequency band is no less than the predetermined value.

6. The vehicle control device according to claim 1, wherein:
the vibration information detection device includes an acceleration sensor which is installed in the seat or the vehicle body and which is configured to detect acceleration in an up-down direction; and
the processor is configured to calculate acceleration, velocity, or displacement amount of the seat, in the up-down direction, as the vibration of the seat, based on the detection results of the vibration information detection device.

7. The vehicle control device according to claim 1, wherein:
the vibration information detection device is configured to detect information related to vehicle speed as the information relating to the vibration of the seat; and
the processor is configured to determine that the vibration of the seat is less than the predetermined value when the vehicle speed is less than a predetermined vehicle speed.

8. The vehicle control device according to claim 1, wherein:
the vibration information detection device is configured to detect, as the information relating to the vibration of the seat, information relating to a planned traveling road surface that is a road surface over which an object wheel is planned to travel; and
the processor is configured to,
based on the information relating to the planned traveling road surface, compute a prediction value of the vibration of the seat when the object wheel travels over the planned traveling road surface, and determine whether the prediction value is less than the predetermined value, and
when determining that the specific occupant is asleep or falling asleep, and determining that the prediction value is less than the predetermined value, control the active suspension such that the vibration of the seat when the object wheel travels over the planned traveling road surface is no less than the predetermined value.

9. The vehicle control device according to claim 1, wherein:
the drowsiness detection device is an image sensor configured to perform image-capturing of the occupant;
at least one of the drowsiness detection device and the processor is configured to determine a drowsiness level of the occupant based on image-captured data of the occupant;
the drowsiness level includes at least three stages of asleep, falling asleep, and not asleep; and
the processor is configured to determine whether the occupant is asleep or falling asleep, based on the drowsiness level.

10. The vehicle control device according to claim 1, wherein:
the drowsiness detection device is configured to transmit a sleep onset signal indicating that the occupant is falling asleep to the controller in response to an operation performed by the occupant; and
the processor is configured to determine that the occupant is falling asleep when the sleep onset signal is received from the drowsiness detection device.

* * * * *